United States Patent [19]

Cousins

[11] 4,367,897
[45] Jan. 11, 1983

[54] ADJUSTABLE SEAT FOR THE HANDICAPPED

[76] Inventor: Steven J. Cousins, 27 Stag Leys, Ashtead, Surrey, England, KT21 2TF

[21] Appl. No.: 220,697

[22] Filed: Dec. 29, 1980

[51] Int. Cl.³ .............................................. A47C 3/00
[52] U.S. Cl. ................................. 297/284; 297/458; 297/460
[58] Field of Search ............... 297/452, 284, 458, 459, 297/460, 464

[56] References Cited

U.S. PATENT DOCUMENTS

| | | | |
|---|---|---|---|
| 1,844,753 | 2/1932 | Gardiner | 297/459 X |
| 3,490,084 | 1/1970 | Schuster | 297/284 X |
| 3,706,473 | 12/1972 | Mullen | 297/456 |
| 3,790,150 | 2/1974 | Lippert | 297/452 X |
| 3,877,750 | 4/1975 | Scholpp | 297/284 |
| 3,899,797 | 8/1975 | Gunst | 297/456 |
| 4,192,547 | 3/1980 | Geier | 297/458 |
| 4,295,683 | 10/1981 | Dubbink et al. | 297/458 X |

Primary Examiner—Francis K. Zugel
Attorney, Agent, or Firm—Fulwider, Patton, Rieber, Lee & Utecht

[57] ABSTRACT

A seat has a shapeable matrix which is constructed of a multiplicity of modular units arranged in longitudinal and transverse rows. The modular units have passageways extending therethrough and contact surfaces which surround open ends of the passageways. Flexible members extend longitudinally through the passageways of the modular units of each row to opposite edges of the matrix. Anchors hold ends of the flexible members to marginal edges of the matrix and tension-applying devices fitted to the members along marginal edges of the matrix allow the modular units to be clamped together so that the contact surfaces are held against one another initially at a pressure allowing the matrix to be contoured to fit selected portions of the human body and subsequently at a greater pressure thereby maintaining the matrix in its contoured shape.

7 Claims, 11 Drawing Figures

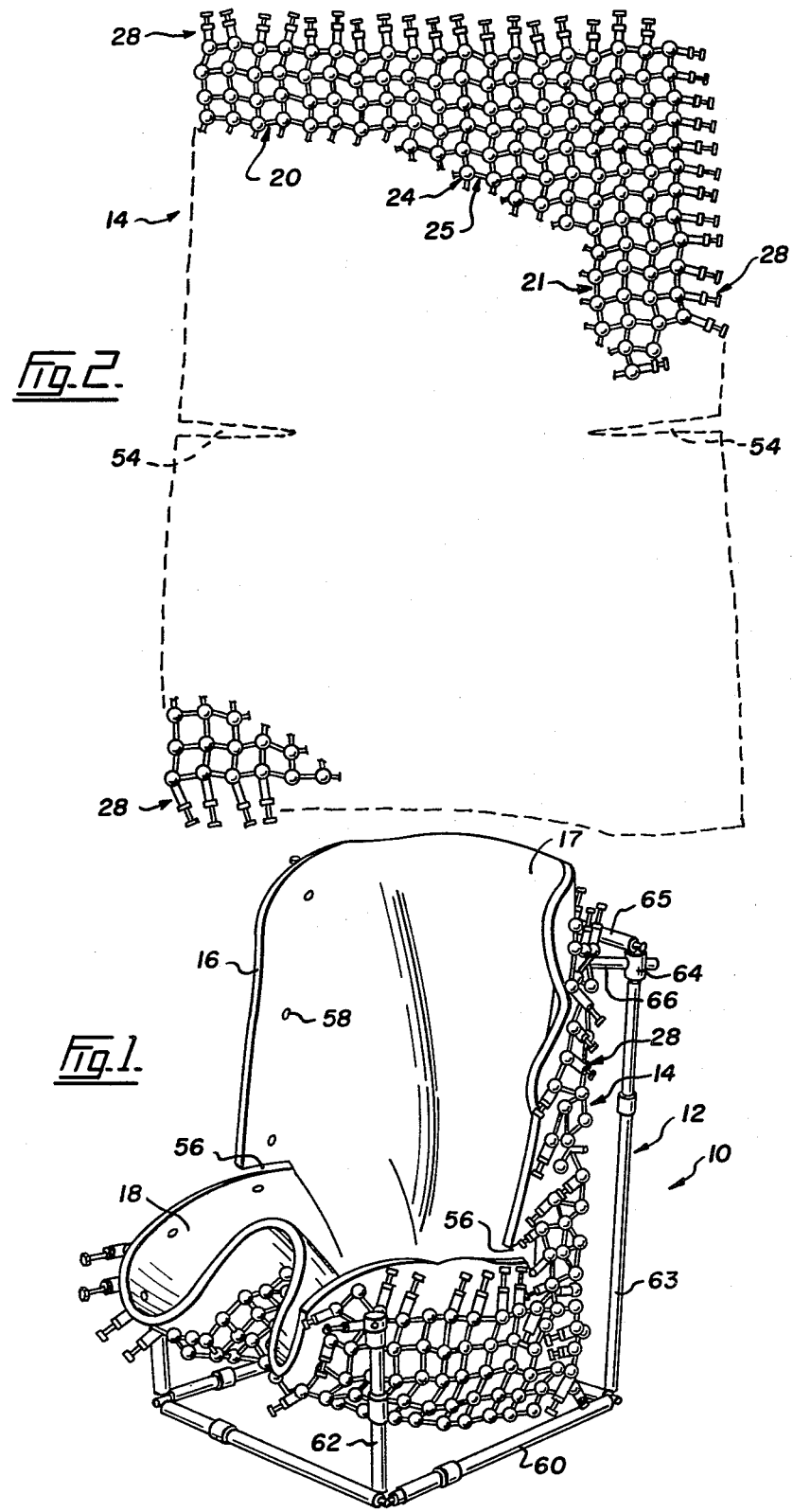

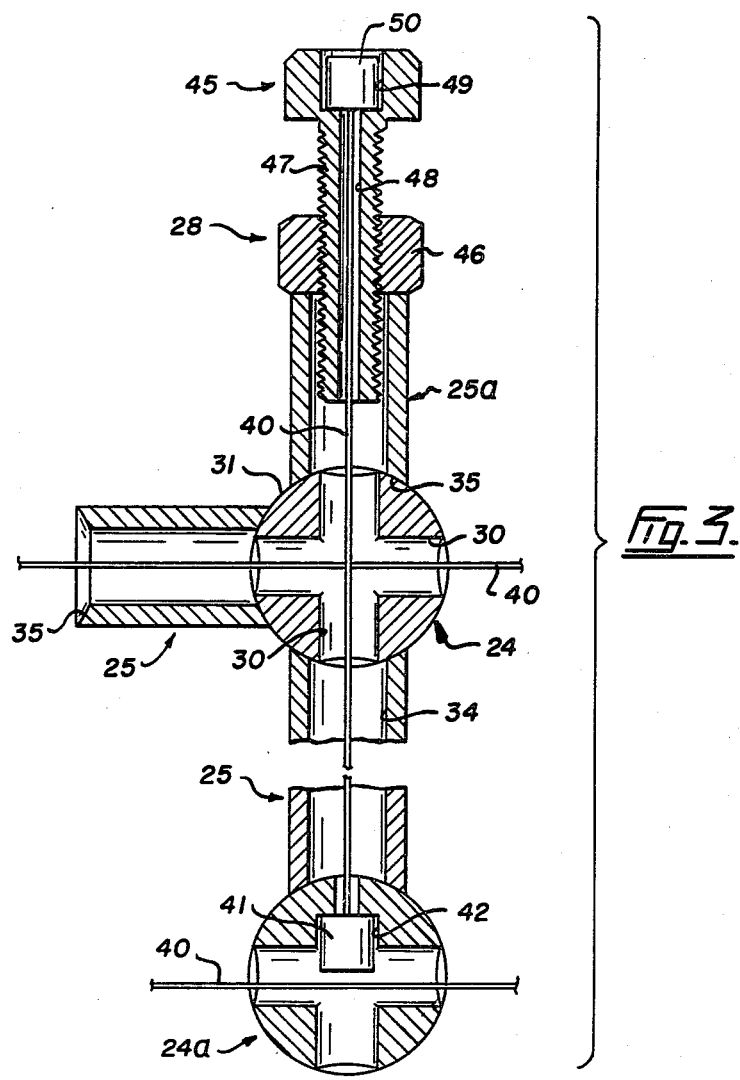
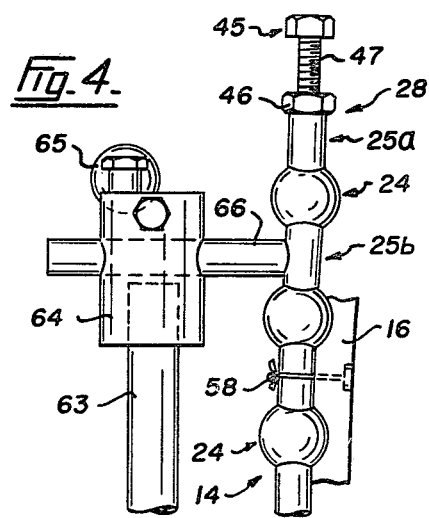

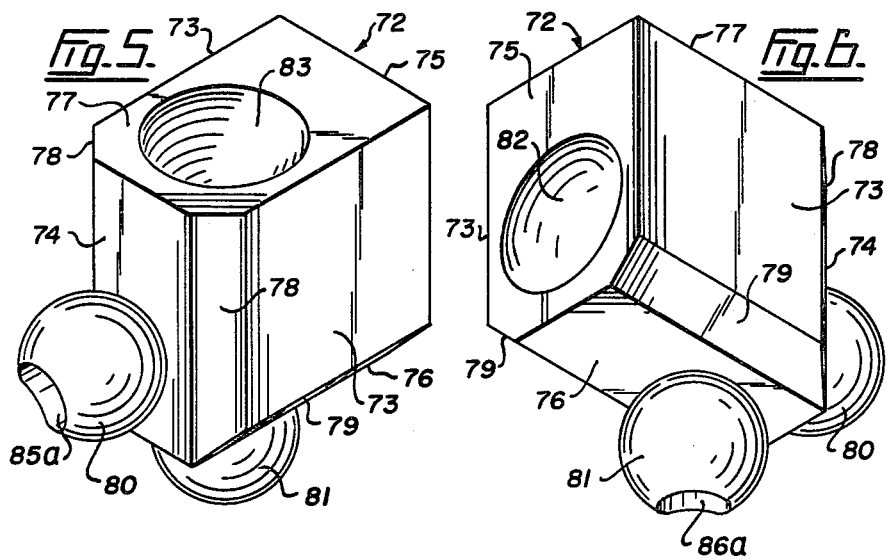
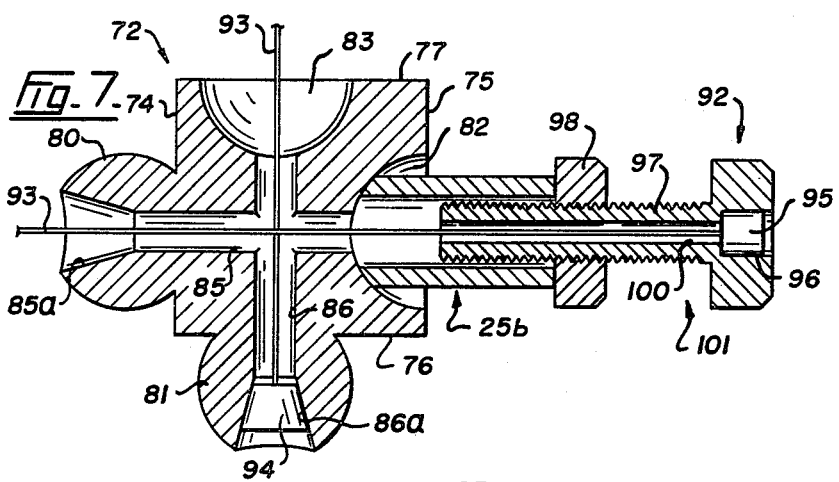
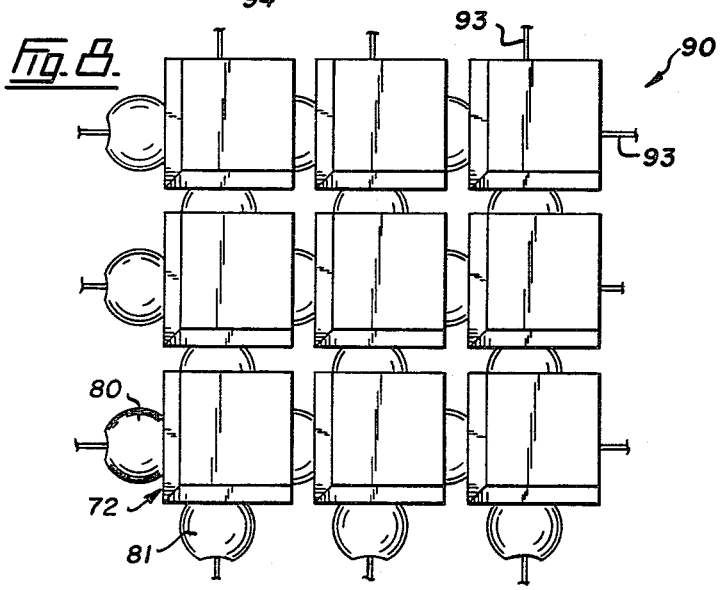

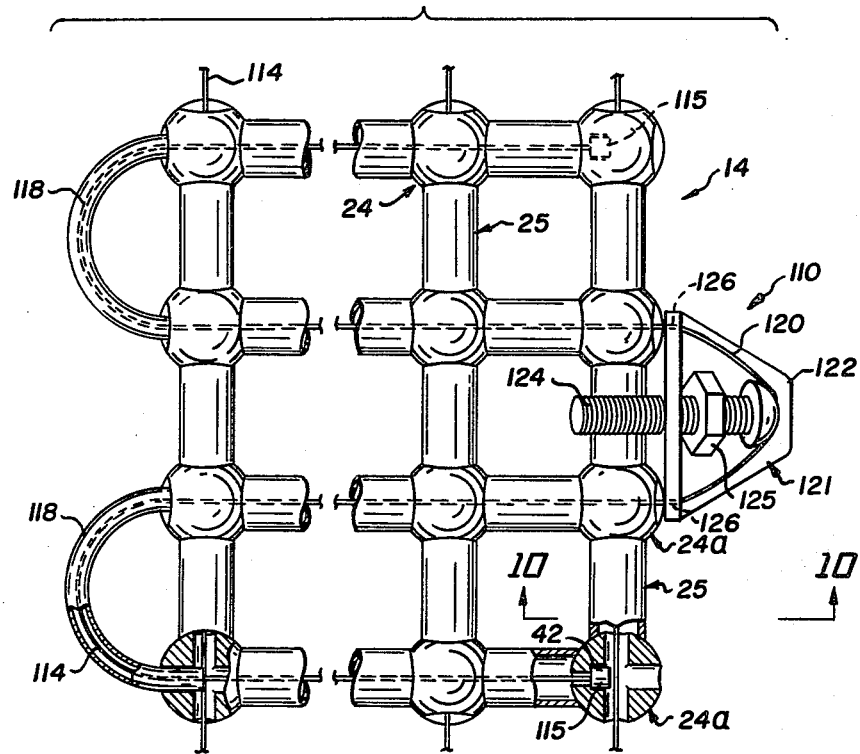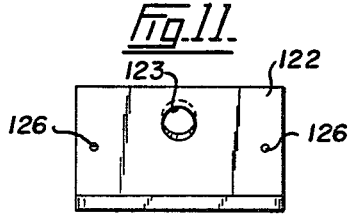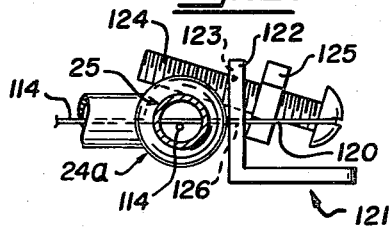

ADJUSTABLE SEAT FOR THE HANDICAPPED

BACKGROUND OF THE INVENTION

This invention relates generally to supportive seating for those who are handicapped and more particularly to a shapeable matrix which can be molded to fit the head, back, buttocks and upper legs of an adult and particularly a child.

Many disabled children such as those suffering from cerebral palsy and muscular dystrophy for example, need additional support when occupying a wheelchair otherwise they cannot remain erect or properly seated and may even go into spasm with the result that they fall or at least collapse into an uncomfortable and sometimes dangerous position if not securely strapped into the chair. Improperly seated children tend to develop pressure sores and there is a risk of increased spinal deformities and respiration difficulties which makes it risky to leave a disabled child unattended in a conventional wheelchair or the like.

There are a number of chairs presently available which are designed so that the shape of the seat and back portions of the chair can be altered to make an able bodied person, and particularly an adult, more comfortable and less subjected to fatigue but these are of little help when it comes to providing the type of seating which is required by disabled adults and children. When attempts are made to incorporate some of the structural features of known chairs into a specialized seat for a disabled person, it is generally found that such a seat is expensive and requires a considerable amount of the time of a skilled technician attempting to fabricate and adjust the seat to meet the needs of particular individuals. The result has been that some treatment and rehabilitation centers have resorted to making seat inserts for conventional chairs. Such inserts are often cast of plaster or are otherwise formed to fit a particular child and are discarded and replaced periodically as the intended user grows or his condition changes.

SUMMARY OF THE INVENTION

The present invention provides a seating arrangement which can be placed on a conventional chair to accommodate a disabled child or adult. The arrangement includes a support structure which is moldable to fit the body of the seated person. In one condition, the support structure is quite flexible and the shaping or molding can be carried out with speed and precision. Once the structure is molded as required, a simple adjustment locks the support structure in its contoured shape. It is a simple matter to readjust the seat as necessary as might be required to accommodate someone who is growing or whose condition is changing.

BRIEF DESCRIPTION OF THE DRAWINGS

FIG. 1 is a perspective plan view an adjustable seat constructed in accordance with the present invention, FIG. 2 is a plan view of a flattened matrix of the seat, FIG. 3 is an enlarged vertical section showing modular units used to construct the matrix, FIG. 4 is a fragmentary side elevation showing an arrangement for securing the matrix to a support frame of the seat, FIGS. 5 and 6 are perspective views showing opposite sides of a modular unit forming another embodiment of the present invention, FIG. 7 is an enlarged vertical section of the embodiment shown in FIGS. 4 and 5, FIG. 8 is a plan view of a portion of a matrix constructed of units shown in FIG. 7, FIG. 9 is a fragmentary plan view showing the matrix as constructed using the units shown in FIGS. 1 to 4 and fitted with another tensioning means, FIG. 10 is a vertical section taken on the line 10—10 of FIG. 9, and FIG. 11 is a front elevation showing a presser plate of the FIG. 9 tensioning means.

DESCRIPTION OF THE PREFERRED EMBODIMENTS

Referring to the drawings, the numeral 10 in FIG. 1 indicates generally an adjustable seat constructed in accordance with the present invention. The seat 10 is provided with a suitable support frame 12 which carries a shapeable matrix 14. A flexible pad 16 is provided on one side of the matrix and this cushioning member is shaped along with the matrix to provide the present seat with a back portion 17 and a seat portion 18.

The shapeable matrix generally indicated at 14 is shown in FIG. 2 as it would appear if laid out on a flat surface. This arrangement shows best that the substantially rectangular matrix has longitudinal and transverse rows 20 and 21 which form a grid-like panel. The rows are assembled using a large number of modular units which, in this instance, consist of ball elements 24 preferably formed of plastic ⅜th of an inch in diameter and tube elements 25 which are ⅜th of an inch long and also made of plastic. The ball and tube elements are held together by a tensioning means 28 which will be described in detail later.

Referring now to FIG. 3, each ball element 24 will be seen to have holes or passageways 30 which are disposed at right angles to one another. The passageways join or intersect in the exact center of the ball element. The areas on the outer periphery of the ball element between the passageways provide convex surfaces 31 which are contacted by the ends of the tube elements 25.

FIG. 3 also shows that each tube element 25 has a bore or passageway 34. The opposite ends of the cylindrical element 25 are concaved or inwardly dished to provide contact surfaces 35 conforming to the curvature of the convex contact surfaces 31 on the ball elements 24.

There is one tensioning means generally indicated at 28 for each of the longitudinal and transverse rows 20 and 21 of the shapeable matrix. As best shown in FIG. 3, each tensioning means comprises a flexible member 40 which preferably is a length of relatively small-diameter cable formed of stainless steel strands. The elements 24 and 25 are threaded like beads on the flexible member or cable 40, in other words, the cable extends through one of the passageways 30 of each ball element as well as the passageways 34 of the adjoining tube elements. The two modular units of course, are arranged alternately along each row. Secured to one end of the cable 40 is a small cylindrical anchor knob 41 which is lodged in a ball element 24a modified to the extent that it is provided with a recess 42 for seating the knob. Similar modified ball elements 24a are located where required along the marginal edges of the matrix to receive the anchor knobs of other cables.

Arranged along other marginal edges of the shapeable matrix, are tension-applying devices 45 of the means 28, which devices are used to tighten the cables 40. Each device 45 comprises a modified tube element 25a which is fitted with a nut 46. A bolt 47 having a through bore 48 is fitted to the nut 46 to extend into the element 25a. The head of this bolt is provided with a recess 49 in which a pull knob 50 is seated, this knob being secured to one end of the cable 40. matrix 14. The cables 40 extend along the rows and provide a wire mesh core for the matrix. The ball and tube elements which make up each row are movable relative to one another and, by adjustment of the bolts 47, appropriate tension can be applied to the cables and therefore the rows so as to vary the flexibility of the matrix 14 as required.

Referring again to FIG. 2, the matrix 14 when placed flat will be seen to have aligned slots 54 which extend a short distance into opposite side edges of the substantially rectangular panel. These slots divide the matrix into two portions which may be approximately of equal size. When these portions are folded at right angles to one another and are molded to provide the seat portions 17 and 18 shown in FIG. 1, the slots 54 ensure that there are no bulges or unsightly overlapping at the sides of the seat. The side edges of the inwardly-tapering slots 54 may be as much as 90° apart depending on the proposed shape shaping of the matrix but, in any case, some of the cables 40 terminate along the side edges of the slots. Where a cable terminates at a side edge of a slot, the terminal end of that cable is fitted with an anchor knob 41 and there is a modified ball element 24a to receive that knob. The opposite end of that particular cable is fitted with a tension-applying device 45. Otherwise the cables extend from one marginal edge of the matrix to another as shown in FIG. 2. Most of the devices 45 are located on the same marginal or side edges of the matrix but this is done mainly to make the tensioning operation faster and easier to perform and other of the devices may be located where require.

The flexible cushioning pad generally indicated at 16 preferably is a foam rubber panel slightly larger than the matrix 14. Cut-outs 56, see FIG. 1, are provided at the sides of the pad 16 to correspond to the slots 54 in the matrix and which permit a similar folding action. A vinyl lacquer is sprayed over at least the uppermost surface of the pad to create a waterproof finish as flexible as the foam pad itself. The pad 16 is secured to the matrix at widely-spaced intervals, for example, it may be releasably attached along side edges of the two layers by means of ties 58 which appear in FIG. 1 and are shown in greater detail in FIG. 4.

In order to carry the padded matrix, the support frame generally indicated at 12 is constructed of lengths of aluminum tubing which are connected together to provide a horizontal base 60. The front and rear corners 62 and 63 are mounted on this base. The upper end of the four corner posts are each fitted with a cap 64. A cross bar 65 extends between the caps on the rear corner posts of the frame. The caps on the short front corner posts 62 as well as those on the relatively long rear corner posts 63 each carry a horizontally disposed hanger 66 which extends inwardly of the base frame. The matrix is suspended from these hangers out of contact with the remainder of the frame. Preferably, this attachment of the matrix to the support frame 60 is by the arrangement shown in FIG. 4 where one end of each hanger 66 will be seen to have secured thereto a modified tube element 25b. The modified elements 25b replace four of the elements 25 which form the matrix and the construction and arrangement of the assembly is such that the back portion 17 and the seat portion 18 are supported near their uppermost and foremost corners respectively with the remainder of the structure standing clear of the support frame 12.

The seat 10 is primarily intended for exclusive use by a particular individual, for example a handicapped child requiring additional support in order to maintain a proper seated position. To fit the seat to such a child, the tensioning means 28 are adjusted so that the elements 24 and 25 can move relative to one another when a reasonable amount of force is applied thereto. The matrix 14 is roughly molded to shape whereupon the child is placed on the seat to allow the final shaping and adjusting to be done. This is done by hand with the child receiving temporary support, the technician responsible for the fitting applying pressure to various parts of the matrix so as to mold it to the legs, thighs, buttocks, back and if necessary the head of the occupant. Once the required shape for the panel is arrived at, the several tension-applying devices 45 are tightened to the extent that the contact surfaces 31 and 35 are frictionally locked together and no relative movement can take place between the ball and tube elements. The handicapped child now is supported so that he can maintain a proper seated position without the need for restraining straps or the like. The adjustable seat 10 can be placed on a wheelchair or elsewhere if height or mobility is required. Thus, maximum seating support is provided without preventing the child from wiggling about to some extent as his condition oftens requires and which is necessary in muscle tone and other functional use of the limbs is to be maintained.

Referred now to the embodiment of the invention shown in FIGS. 5 to 8, a modular unit is shown which comprises a block element 72 of plastic or the like. The oblong block element 72 has two side faces 73, side edges 74 and 75, and end edges 76 and 77. At the junction of the plane faces 73 and the side edge 74, the block element has bevels 78. Other bevels 79 are provided where the faces 73 meet the end edge 76. Integrally formed with the block element to project outwardly of the side edge 74, is a ball connector 80. Similarly, the end edge 76 has an integral ball connector 81. The side edge 75 and end edge 77 are provided with semi-spherical socket connectors 82 and 83 respectively. The block element is provided with intersecting passageways 85 and 86 having longitudinal axes which extend through the centers of the ball and socket connectors. The passageways 85 and 86 connect with outwardly-tapering recesses 85a and 86a which are formed in the ball connectors 80 and 81.

The modular block elements are assembled to form a matrix which is generally indicated at 90 in FIG. 8. Each block element is connected to adjoining elements with the ball connectors 80 and 81 seated in the socket connectors 82 and 83 so that the adjoining faces of the connectors provide sliding contact surfaces. The matrix assembly is shown held together by tensioning means 92, see FIGS. 7 and 8. As shown best in FIG. 7, each means 92 comprises a length of cable 93 which is fitted at one end with an anchor knob 94. This knob is tapered to seat in one of the correspondingly tapered recesses in a ball connector located at a marginal edge of the matrix, i.e., the recess 86a as shown in FIG. 7. The opposite ends of the cables are each fitted with a pull knob 95 which is lodged in a recess 96 formed in a bolt 97. A nut 98 on a modified tube element 25b meshes with the bolt 97, the tube element being pivotally supported in a socket connector 82 and the cable 93 extending through the bore 100 of the bolt as well as through the aligned passageways 85 of the block elements. Thus, the identical block elements 72 can be assembled as the shapeable matrix 90 which has a wire-mesh core formed by the cables 93. The bolt 97 and nut 98 combine to provide a tension-applying device 101 for the matrix 90.

The matrix 90 is also cushioned by means of a pad 16 which is secured thereto in the manner previously described. A frame 12 supports the padded matrix 90 in a position where it can be molded to fit a particular handicapped person. The fitting or contouring of the seat and back portions is done as previously described with the tensioning means 92 slack so that relative movement can take place between adjoining block elements. Because of the ball and socket connection between the elements and the presence of the levels 78 and 79, sufficient clearance is provided to allow the elements to move in this manner when interconnected by the slacked cables. Once the desired shape has been arrived at, the bolts 97 are tightened so that the block elements are unable to move relative to one another and the adjustable seat is then ready for use in supporting the person for which it is fitted in a wheelchair or elsewhere.

FIGS. 9 to 11 show another embodiment of the tensioning means which is generally indicated at 110. This means 110 can be used on either the matrix 14 or 90 although for convenience, it is shown installed on the former matrix. The means 110 comprises a plurality of cables 114 which extend through the matrix to bind the ball and the tube elements, 24 and 25 together as a moldable assembly of parts. Each cable 114 is fitted at its opposite ends with anchor knobs 115 which are lodged in the recesses 42 of ball elements 24a spaced along the same marginal edge of the matrix. Along the opposite marginal edge, there are return tubes 118 which are semi-circular so as to extend between adjacent rows of the matrix as shown in FIG. 9. The two ends of this tube may be entered into recesses 42 and, preferably, the bore of the tube is in line with a suitable low friction material (not shown) which will allow the cable to slide freely through the tube.

The cable 114 is laced through the matrix as shown in FIG. 9 and, between the anchor knobs 115, the cable is formed into a bight 120 which extends over a tension applying device 121. This device comprises a presser plate 122 which bears against two adjacent ball elements 24a. The right angle plate 122 has a centrally-disposed hole 123 through which a bolt 124 slidably extends, the slotted head of the bolt providing a seat for the bight of the cable. A nut 125 on the bolt abuts one flange of the presser plate and the plate is provided with holes 126 which allow the cable to slide freely therethrough.

It will be apparent that the means 110 allows simultaneous tensioning at least four rows of the matrix. Each cable 114 with its single device 121 allows a corresponding number of rows to be tightened and, of course, the several devices can be located along adjacent marginal edges of the matrix. This construction and arrangement reduces the time and effort which is required to fit the seat to accommodate a particular individual and there is a corresponding saving in the cost of material.

From the foregoing, it will be appreciated that an adjustable seat fitted with either matrix and the preferred tensioning means can readily be shaped to support someone with special supportive requirements. The seat can be adjusted periodically with equal ease and speed as might be necessary for a growing child or someone whose need for support in a particular area would change from time to time.

I claim:

1. An adjustable seat comprising a support frame, a shapeable matrix mounted on the support frame and being formed of a multiplicity of modular units arranged in longitudinal and transverse rows, said modular units having passageways extending therethrough and contact surfaces surrounding open ends of said passageways, flexible members extending through the passageways of the modular units of each row to marginal edges of the shapeable matrix, anchor means securing corresponding ends of the flexible members to marginal edges of the shapeable matrix, and tension-applying devices on marginal edges of the shapeable matrix for tensioning the flexible members whereby the contact surfaces of adjoining modular units are frictional drawn together initially at a pressure allowing the shapeable matrix to be contoured to fit and properly brace selected parts of the body of a seated occupant and subsequently at a greater pressure thereby maintaining the shapeable matrix in its contoured condition.

2. An adjustable seat as claimed in claim 1, in which said modular units comprise ball and tube elements arranged alternately along each row, said ball elements each having two of the passageways extending therethrough at right angles to one another and joining at the centre of said element, said contact surfaces of the ball elements surrounding opposite ends of each passageway, and said contact surfaces of the tube elements being opposite ends of the tube elements shaped to conform to the contact surfaces of adjoining ball elements.

3. An adjustable seat as claimed in claim 2, and including a flexible cushion covering the shapeable matrix.

4. An adjustable seat as claimed in claim 1, in which said modular units are block elements each having two of the passageways extending therethrough at right angles to one another and joining at the centre of said element, said block elements each having two adjacent faces each provided with an outwardly-projecting ball connector through which one of the passageways extends, and each block element having two other adjacent faces each provided with an inwardly-dished socket connector through which one of the passageways extends.

5. An adjustable seat as claimed in claim 4, in which said two adjacent faces from which the ball connectors project have bevelled edges to provide clearance between adjoining block elements.

6. An adjustable seat as claimed in claim 5, and including a flexible cushion covering the sheapable matrix.

7. An adjustable seat as claimed in claim 2, in which said tension-applying devices are fewer in number than the anchor means and are located along marginal edges of the shapeable matrix whereby the flexible members of several rows are tensionable by each tensionapplying device.

* * * * *